United States Patent
Yamada

(10) Patent No.: US 9,192,163 B2
(45) Date of Patent: Nov. 24, 2015

(54) PEST CONTROL COMPOSITION

(71) Applicant: Sumitomo Chemical Company, Limited, Tokyo (JP)

(72) Inventor: Masahiro Yamada, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/354,304

(22) PCT Filed: Dec. 12, 2012

(86) PCT No.: PCT/JP2012/082850
§ 371 (c)(1),
(2) Date: Apr. 25, 2014

(87) PCT Pub. No.: WO2013/099713
PCT Pub. Date: Jul. 4, 2013

(65) Prior Publication Data
US 2014/0315998 A1    Oct. 23, 2014

(30) Foreign Application Priority Data

Dec. 28, 2011   (JP) ................................. 2011-289276

(51) Int. Cl.
A61K 31/275   (2006.01)
A61K 31/21    (2006.01)
A01N 53/00    (2006.01)

(52) U.S. Cl.
CPC ....................... A01N 53/00 (2013.01)

(58) Field of Classification Search
None
See application file for complete search history.

(56) References Cited

U.S. PATENT DOCUMENTS

| | | | |
|---|---|---|---|
| 6,177,465 B1 | 1/2001 | Tanaka | |
| 6,294,577 B1 * | 9/2001 | Vander Meer et al. | 514/547 |
| 2003/0195119 A1 | 10/2003 | Mori | |
| 2009/0081132 A1 | 3/2009 | Yamada | |
| 2010/0016384 A1 | 1/2010 | Sembo | |
| 2010/0047183 A1 | 2/2010 | Tanaka | |
| 2010/0113594 A1 | 5/2010 | Yamada et al. | |
| 2010/0130602 A1 | 5/2010 | Yamada et al. | |
| 2010/0210698 A1 | 8/2010 | Tanaka | |
| 2012/0225917 A1 | 9/2012 | Yamada et al. | |
| 2013/0171076 A1 | 7/2013 | Yamada | |
| 2013/0172409 A1 | 7/2013 | Harada et al. | |

FOREIGN PATENT DOCUMENTS

| | | |
|---|---|---|
| JP | S59-212403 A | 12/1984 |
| JP | H06-305904 A | 11/1994 |
| JP | 2001-010907 A | 1/2001 |
| JP | 2004-002363 A | 1/2004 |
| JP | 2008-201731 A | 9/2008 |
| JP | 2008-273944 A | 11/2008 |
| JP | 2008-273945 A | 11/2008 |
| JP | 2008-273946 A | 11/2008 |
| JP | 2008-273947 A | 11/2008 |
| JP | 2009-062299 A | 3/2009 |
| JP | 2009-079040 A | 4/2009 |
| JP | 2009-091353 A | 4/2009 |
| JP | 2010-077073 A | 4/2010 |
| JP | 2011-126875 A | 6/2011 |
| JP | 2011-132199 A | 7/2011 |
| JP | 2011-132200 A | 7/2011 |
| JP | 2011-132201 A | 7/2011 |
| JP | 2011-144150 A | 7/2011 |
| JP | 2011-144151 A | 7/2011 |
| JP | 2011-148760 A | 8/2011 |
| JP | 2012-077070 A | 4/2012 |
| JP | 2012-082192 A | 4/2012 |
| WO | 2008123573 A2 | 10/2008 |
| WO | 2009031692 A2 | 3/2009 |
| WO | 2013099715 A1 | 7/2013 |

OTHER PUBLICATIONS

Written Opinion issued Feb. 12, 2013 in Int'l Application No. PCT/JP2012/082850.
International Search Report issued on Feb. 12, 2013 in Int'l Application No. PCT/JP2012/082850.

* cited by examiner

*Primary Examiner* — Jeffrey S Lundgren
*Assistant Examiner* — Michael Schmitt
(74) *Attorney, Agent, or Firm* — Panitch Schwarze Belisario & Nadel LLP

(57) ABSTRACT

A pest control composition is provided having an excellent control effect on pests and containing an ester compound represented by the following formula (1) and diethyl adipate. A method is also provided for controlling pests including applying the pest control composition to pests or habitats of pests.

(1)

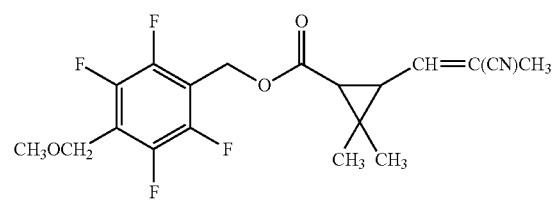

3 Claims, No Drawings

PEST CONTROL COMPOSITION

CROSS-REFERENCE TO RELATED APPLICATION

This application is a Section 371 of International Application No. PCT/JP2012/082850, filed Dec. 12, 2012, which was published in the English language on Jul. 4, 2013, under International Publication No. WO 2013/099713 A1, and the disclosure of which is incorporated herein by reference.

TECHNICAL FIELD

The present invention relates to a pest control composition and a method for controlling pests.

BACKGROUND ART

An ester compound represented by the following formula (1) has been known to have a control effect on noxious arthropods (for example, see Patent Document 1).

CITATION LIST

Patent Literature

Patent Literature 1: JP-A-2004-2363

SUMMARY OF INVENTION

Technical Problem

An object of the present invention is to provide a pest control composition having an excellent control effect on noxious animals and a method for controlling noxious animals.

Solution of Problem

The present inventor has intensively studied in order to find a composition having an excellent control effect, and found that a composition containing an ester compound represented by the following formula (1) and diethyl adipate has an excellent control effect on noxious animals, and thus the present invention has been accomplished.

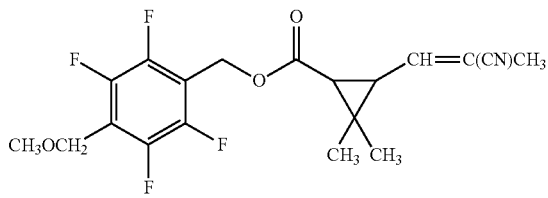

(1)

Specifically, the present invention includes the following inventions:
[1] A pest control composition comprising an ester compound represented by the formula (1) and diethyl adipate.
[2] The pest control composition according to [1], wherein a content ratio of the ester compound represented by the formula (1) to the diethyl adipate is from 4:1 to 1:300 by weight ratio.
[3] The pest control composition according to [1], wherein the content ratio of the ester compound represented by the formula (1) to the diethyl adipate is from 1:1 to 1:100 by weight ratio.
[4] A method for controlling pests comprising applying the pest control composition according to any one of [1] to [3] to pests or habitats of pests.

Effect of Invention

The pest control composition of the present invention has an excellent effect in controlling pests.

DESCRIPTION OF EMBODIMENTS

The pest control composition of the present invention contains an ester compound represented by the formula (1) (hereinafter, referred to as "the present ester compound") and diethyl adipate.

The present ester compound can be produced, for example, by the method described in JP-A-2004-2363 or the like.

The present ester compound has isomers based on two asymmetric carbon atoms on the cyclopropane ring and based on a double bond of a substituent substituted on the cyclopropane ring. In the present invention, an ester compound containing the active isomers in any ratios can be used.

Examples of the present ester compound include:
[2,3,5,6-tetrafluoro-4-(methoxymethyl)phenyl]methyl (1R)-3-(2-cyano-1-propenyl)-2,2-dimethylcyclopropanecarboxylate,
[2,3,5,6-tetrafluoro-4-(methoxymethyl)phenyl]methyl (1R)-trans-3-(2-cyano-1-propenyl)-2,2-dimethylcyclopropanecarboxylate,
[2,3,5,6-tetrafluoro-4-(methoxymethyl)phenyl]methyl (1R)-cis-3-(2-cyano-1-propenyl)-2,2-dimethylcyclopropanecarboxylate,
[2,3,5,6-tetrafluoro-4-(methoxymethyl)phenyl]methyl (1R)-trans-3-((E)-2-cyano-1-propenyl)-2,2-dimethylcyclopropanecarboxylate, and
[2,3,5,6-tetrafluoro-4-(methoxymethyl)phenyl]methyl (1R)-trans-3-((Z)-2-cyano-1-propenyl)-2,2-dimethylcyclopropanecarboxylate.

As the diethyl adipate, those commercially available or produced by a known method can be used.

Examples of pests against which the pest control composition of the present invention exhibits a controlling effect (insecticidal effect, knockdown effect, repellent effect, etc.) include noxious arthropods such as insect pests and acarine pests. Specific examples thereof include the followings.

Lepidoptera vermin: Pyralidae such as *Chilo suppressalis, Cnaphalocrocis medinalis*, and *Plodia interpunctella*; Noctuidae such as *Spodoptera litura, Pseudaletia separata*, and *Mamestra brassicae*; Pieridae such as *Pieris rapae*; Tortricidae such as *Adoxophyes orana*; Carposinidae; Lyonetiidae; Lymantriidae; Antographa; *Agrotis* spp. such as *Agrotis segetum* and *Agrotis ipsilon; Helicoverpa* spp.; *Heliothis* spp.; *Plutella xylostella; Parnara guttata; Tinea pellionella; Tineola bisselliella*; etc.

Diptera vermin: *Culex* spp. such as *Culex pipiens pallens* and *Culex tritaeniorhynchus; Aedes* spp. such as *Aedes aegypti* and *Aedes albopictus; Anopheles* spp. such as *Anopheles sinensis*; Chironomidae; Muscidae such as *Musca domestica, Muscina stabulans*, and *Fannia canicularis*; Calliphoridae; Sarcophagidae; Anthomyiidae such as *Delia platura* and *Delia antiqua*; Tephritidae; Agromyzidae; Drosophilidae; Psychodidae; Phoridae; Tabanidae; Simuliidae; *Culicoides*; Ceratopogonidae; etc.

Dictyoptera vermin: *Blattella germanica, Periplaneta fuliginosa, Periplaneta americana, Periplaneta brunnea, Blatta orientalis*, etc.

Hymenoptera vermin: Formicidae, Vespidae, Bethylidae, Tenthredinidae such as *Athalia rosae ruficornis*, etc.

Siphonaptera vermin: *Ctenocephalides canis, Ctenocephalides felis, Pulex irritans*, etc.

Anoplura vermin: *Pediculus humanus, Pthirus pubis, Pediculus humanus capitis, Pediculus humanus corporis*, etc.

Isoptera vermin: *Reticulitermes speratus, Coptotermes formosanus*, etc.

Hemiptera vermin: Delphacidae such as *Laodelphax striatellus, Nilaparvata lugens*, and *Sogatella furcifera*; Deltocephalidae such as *Nephotettix cincticeps* and *Nephotettix virescens*; Aphididae; Pentatomidae; Aleyrodidae; Coccoidea; Cimicidae such as *Cimex lectularius*; Tingidae; Psyllidae; etc.

Coleoptera vermin: *Attagenus japonicus; Anthrenus verbasci; Diabrotica* spp. such as *Diabrotica virgifera virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus, Anthonomus grandis*, and *Callosobruchus chinensis*; Tenebrionidae such as *Tenebrio molitor* and *Tribolium castaneum*; Chrysomelidae such as *Oulema oryzae, Phyllotreta striolata*, and *Aulacophora femoralis; Anobiidae; Epilachna* spp. such as *Epilachna vigintioctopunctata*; Lyctidae; Bostrychidae; Cerambycidae; *Paederus fuscipes*; etc.

Thysanoptera vermin: *Thrips palmi, Frankliniella occidentalis, Thrips hawaiiensis*, etc.

Orthoptera vermin: Gryllotalpidae, Acrididae, etc.

Acarina: Dermanyssidae such as *Dermatophagoides farinae* and *Dermatophagoides pteronyssinus*; Acaridae such as *Tyrophagus putrescentiae* and *Aleuroglyphus ovatus*; Glycyphagidae such as *Glycyphagus privatus, Glycyphagus domesticus*, and *Glycyphagus destructor*; Cheyletidae such as *Cheyletus malaccensis* and *Cheyletus fortis*; Tarsonemidae; *Chortoglyphus* spp.; Haplochthoniidae; Tetranychidae such as *Tetranychus urticae, Tetranychus Kanzawai, Panonychus citri*, and *Panonychus ulmi*; Ixodidae such as *Haemaphysalis longicornis*; Dermanyssidae such as *Ornithonyssus sylviarum* and *Dermanyssus gallinae*.

In particular, the pest control composition of the present invention has an excellent controlling effect on Diptera vermin, Dictyoptera vermin, and Hymenoptera vermin.

In the pest control composition of the present invention, a content ratio of the present ester compound to the diethyl adipate is generally from 4:1 to 1:300, preferably from 1:1 to 1:100, and more preferably from 1:2 to 1:20 by weight ratio. When two or more kinds of the diethyl adipates are contained in the pest control composition of the present invention, a content ratio of the present ester compound to the total weight of the diethyl adipates is the content ratio of the present ester compound to the diethyl adipate described above.

In the pest control composition of the present invention, a mixture of the present ester compound and the diethyl adipate may be used as it is. However, it is generally used as the following formulations. Examples of the formulations include a solution, an oil solution, an emulsion, a wettable powder, a flowable (aqueous suspension, aqueous emulsion, etc.), a microcapsule, a powder, a granule, a tablet, an aerosol, a carbon dioxide formulation, a heating transpiration formulation (insecticidal incense stick, electric insecticidal mat, liquid absorption wicking-type heating transpiration insecticide, etc.), a piezo-type insecticidal formulation, a heating fumigant (self-burning fumigant, chemical reaction-type fumigant, porous ceramic plate fumigant, etc.), a non-heating transpiration formulation (resin transpiration formulation, paper transpiration formulation, nonwoven fabric transpiration formulation, knit fabric transpiration formulation, sublimable tablet, etc.), a smoking formulation (fogging, etc.), a direct contact formulation (sheet-like contact formulation, tape-like contact formulation, net-like contact formulation, etc.), a ULV formulation, and a poison bait.

As a method for the formulation, the following methods can be exemplified.

(1) A method in which a mixture of the present ester compound and the diethyl adipate is mixed with solid carriers, liquid carriers, gaseous carriers, baits or the like, and if necessary, surfactants and/or other auxiliary agents for formulation are added thereto, followed by processing.

(2) A method in which a base material containing no active ingredient is impregnated with a mixture of the present ester compound and the diethyl adipate.

(3) A method in which the present ester compound, the diethyl adipate and a base material are mixed and then molded.

These formulations generally contain the present ester compound and the diethyl adipate in a total amount of 0.001 to 98% by weight.

Examples of the solid carrier used for the formulation include fine powders and granules of clays (kaolin clay, diatomaceous earth, bentonite, Fubasami clay, acidic white clay, etc.), synthetic hydrated silicon dioxide, talc, ceramics, other inorganic minerals (sericite, quartz, sulfur, activated carbon, calcium carbonate, hydrated silica, etc.) and chemical fertilizers (ammonium sulfate, ammonium phosphate, ammonium nitrate, ammonium chloride, urea, etc.); solid substances at ordinary temperatures (2,4,6-triisopropyl-1,3,5-trioxane, naphthalene, p-dichlorobenzene, camphor, adamantane, etc.); and felts, fibers, cloths, knitted goods, sheets, paper, yarns, foams, porous bodies and multifilaments including one or two or more of wool, silk, cotton, hemp, pulp, synthetic resins (e.g., polyethylene-based resins such as low-density polyethylene resins, linear low-density polyethylene resins, and high-density polyethylene resins; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene-based resins such as propylene homopolymers and propylene-ethylene copolymers; poly-4-methylpentene-1, polybutene-1, polybutadienes, and polystyrenes; acrylonitrile-styrene resins; styrene-based elastomers such as acrylonitrile-butadiene-styrene resins, styrene-conjugated diene block copolymers, and styrene-conjugated diene block copolymer hydrogenated products; fluororesins; acrylic resins such as polymethyl methacrylate; polyamide-based resins such as nylon 6 and nylon 66; polyester-based resins such as polyethylene terephthalate, polyethylene naphthalate, polybutylene terephthalate, and polycyclohexylenedimethylene terephthalate; and porous resins such as polycarbonate, polyacetal, polyacrylsulfone, polyacrylate, hydroxybenzoic acid polyester, polyether imide, polyester carbonate, polyphenylene ether resins, polyvinyl chloride, polyvinylidene chloride, polyurethane, foamed polyurethane, foamed polypropylene, and foamed ethylene), glass, metals, ceramics, and the like.

Examples of the liquid carrier include aromatic or aliphatic hydrocarbons (xylene, toluene, alkylnaphthalene, phenylxylylethane, kerosene, light oil, hexane, cyclohexane, etc.), halogenated hydrocarbons (chlorobenzene, dichloromethane, dichloroethane, trichloroethane, etc.), alcohols (methanol, ethanol, isopropyl alcohol, butanol, hexanol, benzyl alcohol, ethylene glycol, etc.), ethers (diethyl ether, ethylene glycol dimethyl ether, diethylene glycol monomethyl ether, diethylene glycol monoethyl ether, propylene glycol monomethyl ether, tetrahydrofuran, dioxane, etc.), esters (ethyl acetate and butyl acetate), ketones (acetone, methyl ethyl ketone, methyl isobutyl ketone, cyclohexanone, etc.), vegetable oils (soybean oil, cotton seed oil, etc.), vegetable essential oils (orange oil, hyssop oil, lemon oil, etc.), and water.

Examples of the gaseous carrier include butane gas, chlorofluorocarbon gas, liquefied petroleum gas (LPG), dimethyl ether, nitrogen, and carbon dioxide gas.

Examples of the surfactant include alkyl sulfates, alkyl sulfonates, alkylaryl sulfonates, alkylaryl ethers, polyoxyethylenated alkylaryl ethers, sorbitan fatty acid esters, polyoxyethylene sorbitan fatty acid esters, polyethylene glycol ethers, polyhydric alcohol esters, and sugar alcohol derivatives.

Examples of the other auxiliary agents for formulation include sticking agents, dispersants, and stabilizers, and the like. Specific examples thereof include casein, gelatin, polysaccharides (starch, gum arabic, cellulose derivatives, alginic acid, etc.), lignin derivatives, bentonite, saccharides, synthetic water-soluble polymers (polyvinyl alcohol, polyvinyl pyrrolidone, polyacrylic acid, etc.), BHT (2,6-di-tert-butyl-4-methylphenol), and BHA (mixture of 2-tert-butyl-4-methoxyphenol and 3-tert-butyl-4-methoxyphenol).

Examples of a base material of the insecticidal incense stick include mixtures of plant powders such as wood powder and pyrethrum powder and binders such as Tabu powder, starch, and gluten.

Examples of a base material of the electric insecticidal mat include plate-shaped cotton linter and plat-shaped fibril of a mixture of cotton linter and pulp.

Examples of a base material of the self-burning fumigant include combustible exothermic agents such as nitrates, nitrites, guanidine salts, potassium chlorate, nitrocellulose, ethyl cellulose, and wood powder; pyrolysis-promoting agents such as alkali metal salts, alkaline earth metal salts, bichromates, and chromates; oxygen suppliers such as potassium nitrate; combustion supporting agents such as melamine and wheat starch; extenders such as diatomaceous earth; and binders such as synthetic adhesives.

Examples of a base material of the chemical reaction-type fumigant include exothermic agents such as sulfides, polysulfides, and hydrosulfides of alkali metals, and calcium oxide; catalysts such as carbonaceous substances, iron carbide, and activated white clay; organic foaming agents such as azodicarbonamide, benzenesulfonyl hydrazide, dinitropentamethylenetetramine, polystyrenes and polyurethanes; and fillers such as natural fiber pieces and synthetic fiber pieces.

Examples of a resin used for a base material of the resin transpiration formulation or the like include polyethylene-based resins such as low-density polyethylene resins, linear low-density polyethylene resins, and high-density polyethylene resins; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene-based resins such as propylene homopolymers and propylene-ethylene copolymers; poly-4-methylpentene-1, polybutene-1, polybutadienes, and polystyrenes; acrylonitrile-styrene resins; styrene-based elastomers such as acrylonitrile-butadiene-styrene resins, styrene-conjugated diene block copolymers, and styrene-conjugated diene block copolymer hydrogenated products; fluororesins; acrylic acid resins such as polymethyl methacrylate; polyamide-based resins such as nylon 6 and nylon 66; polyester-based resins such as polyethylene terephthalate, polyethylene naphthalate, polybutylene terephthalate, and polycyclohexylenedimethylene terephthalate; and porous resins such as polycarbonate, polyacetal, polyacrylsulfone, polyacrylate, hydroxybenzoic acid polyester, polyether imide, polyester carbonate, polyphenylene ether resins, polyvinyl chloride, polyvinylidene chloride, and polyurethane. These base materials may be used alone or in combination of two or more kinds thereof, and if necessary, plasticizers such as phthalic acid esters (dimethyl phthalate, dioctyl phthalate, etc.), adipic aid esters, and stearic acid may be added to these base materials. The resin transpiration formulation can be obtained by kneading the present ester compound and the diethyl adipate into the base material, followed by molding with injection molding, extrusion molding, press molding, or the like. The obtained resin formulation can also undergo further steps such as molding and cutting, if necessary, to be processed into a form of plate-shaped, film-shaped, tape-shaped, net-shaped, string-shaped, or the like. These resin formulations are processed into, for example, collars for animals, ear tags for animals, sheet formulations, guide strings, and horticultural supports.

Examples of a base material for a poison bait include bait ingredients such as grain powder, vegetable oil, sugar, and crystalline cellulose; antioxidants such as dibutylhydroxytoluene and nordihydroguaiaretic acid; preservatives such as dehydroacetic acid; agents to prevent accidental ingestion by children and pets such as chili pepper powder; and vermin attractive flavors such as cheese flavor, onion flavor, and peanut oil.

In the pest control composition of the present invention, a vermin control agent, a repellent, a synergist or the like may be mixed or used in combination, besides the present ester compound and the diethyl adipate.

Examples of active ingredients of the other vermin control agents that can be mixed or used in combination include the following ingredients.

(1) Synthetic Pyrethroid Compounds acrinathrin, allethrin, beta-cyfluthrin, bifenthrin, cyclopro-thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, [2,3,5,6-tetrafluoro-4-(methoxymethyl)phenyl]methyl 2,2-dimethyl-3-(1-propenyl)cyclopropanecarboxylate, [2,3,5,6-tetrafluoro-4-methylphenyl]methyl 2,2-dimethyl-3-(1-propenyl)cyclopropanecarboxylate, [2,3,5,6-tetrafluoro-4-(methoxymethyl)phenyl]methyl 2,2-dimethyl-3-(2-methyl-1-propenyl)cyclopropanecarboxylate, [2,3,5,6-tetrafluoro-4-(methoxymethyl)phenyl]methyl 2,2,3,3-tetramethylcyclopropanecarboxylate, etc;

(2) Organophosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIPdichlorodiisopropyl ether, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, etc.;

(3) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, aldicarb, etc.;

(4) Nereistoxin Compounds cartap, bensultap, thiocyclam, monosultap, bisultap, etc.;

(5) Neonicotinoid Compounds imidacloprid, nitenpyram, acetamiprid, thiamethoxam, thiacloprid, dinotefuran, clothianidin, etc.;

(6) Benzoylurea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, etc.;

(7) Phenylpyrazole Compounds acetoprole, ethiprole, fipronil, vaniliprole, pyriprole, pyrafluprole, etc.;

(8) Bt Toxin Insecticides

Live spores derived and crystal toxins produced from *Bacillus thuringiesis* and a mixture thereof;

(9) Hydrazine Compounds chromafenozide, halofenozide, methoxyfenozide, tebufenozide, etc.;

(10) Organochlorine Compounds aldrin, dieldrin, dienochlor, endosulfan, methoxychlor, etc.;

(11) Natural Insecticides machine oil, nicotine-sulfate;

(12) Other Insecticides avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, Amilbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calciumpolysulfide, chlordane, DDT, DSP, flufenerim, flonicamid, flurimfen, formetanate, metam-ammonium, metam-sodium, Methyl bromide, Potassium oleate, protrifenbute, spiromesifen, Sulfur, metaflumizone, spirotetramat, pyrifluquinazone, spinetoram, chlorantraniliprole, tralopyril, etc.

Examples of an active ingredient of the repellent include N,N-diethyl-m-toluamide, limonene, linalool, citronellal, menthol, menthone, hinokitiol, geraniol, eucalyptol, indoxacarb, carane-3,4-diol, MGK-R-326, MGK-R-874, and BAY-KBR-3023.

Examples of the synergist include 5-[2-(2-butoxyethoxy)ethoxymethyl]-6-propyl-1,3-benzodioxole, N-(2-ethylhexyl)bicyclo[2.2.1]hept-5-ene-2,3-dicarboxyimide, octachlorodipropyl ether, isobornyl thiocyanoacetate, and N-(2-ethylhexyl)-1-isopropyl-4-methylbicyclo[2.2.2]oct-5-ene-2,3-dicarboxyimide.

The method for controlling pests of the present invention is carried out by applying the pest control composition of the present invention to pests or habitats of pests (plant body, soil, indoor, animal body, etc.).

Specifically, as a method for applying the pest control composition of the present invention, the following methods can be exemplified, and these methods can be appropriately selected depending on the form of the pest control composition of the present invention, the application site, and the like.

(1) A method in which the pest control composition of the present invention is applied as it is to pests or habitats of pests.

(2) A method in which the pest control composition of the present invention is diluted with a solvent such as water and then applied to pests or habitats of pests by spraying.

In this case, the pest control composition of the present invention formulated into an emulsion, a wettable powder, a flowable, a microcapsule or the like is generally diluted so that the total concentration of the present ester compound and the diethyl adipate is 0.01 to 1,000 ppm.

(3) A method in which the pest control composition of the present invention is heated in habitats of pests so that the active ingredients are volatilized.

In this case, the application amount and application concentration of the present ester compound and the diethyl adipate can be appropriately determined depending on the form of the pest control composition of the present invention, the application period, the application site, the application method, the kind of pests, the conditions of damage, and the like.

When the pest control composition of the present invention is used for preventing epidemics, its application amount in terms of the total amount of the present ester compound and the diethyl adipate is generally 0.0001 to 1000 $mg/m^3$ in the case of application in a space, and is 0.0001 to 1000 $mg/m^2$ in the case of application on a plane. The insecticidal incense stick, electric insecticidal mat and the like are used with volatilizing the active ingredients by heating, depending on the form of the formulation. The resin transpiration formulations, paper transpiration formulations, nonwoven transpiration formulations, knit fabric transpiration formulations, sublimable tablets and the like can be used, for example, by allowing the formulations to stand as they are in a space to be applied, or by placing the formulations under air blowing.

Examples of a space where the pest control composition of the present invention is applied for preventing epidemics include a closet, dresser, Japanese style cabinet, cupboard, toilet, bathroom, storeroom, living room, dining room, warehouse, car interior and the like. Further, the composition can also be applied to an outside open space.

When the pest control composition of the present invention is used for controlling ectoparasites on livestock such as cattle, horses, swine, sheep, goat and chickens, and small animals such as dogs, cats, rats and mice, it can be used for the animals by a veterinarily known method. As specific use methods, the composition is administered by way of a tablet, mixing in feed, a suppository, or an injection (intramuscular, subcutaneous, intravenous, intraperitoneal, etc.), when systemic control is intended. On the other hand, the composition is used by the method of spraying an oil solution or aqueous solution, pour-on or spot-on treatment, washing an animal with a shampoo formulation, putting a collar or ear tag made of a resin transpiration formulation to an animal, or the like when non-systemic control is intended. When administered to an animal body, the total amount of the present ester compound and the diethyl adipate is generally in the range from 0.01 to 1000 mg per 1 kg of animal body weight.

EXAMPLES

Hereinafter, the present invention will be described in more detail byway of formulation examples and test examples, but the present invention is not limited only to the following examples. In the following examples, parts mean parts by weight unless otherwise stated.

First, formulation examples of the pest control composition of the present invention will be described. Herein, parts mean parts by weight.

Formulation Example 1

Into an aerosol container, 0.02 parts of the present ester compound, 0.18 parts of the diethyl adipate, and 59.8 parts of Isopar M (isoparaffin-based hydrocarbon, manufactured by Exxon Mobil Corporation) are placed. A valve portion is attached to the aerosol container, and 40 parts of a propellant (liquefied petroleum gas) is filled therein via the valve portion to obtain an aerosol. Here, [2,3,5,6-tetrafluoro-4-(methoxymethyl)phenyl]methyl (1R)-trans-3-(2-cyano-1-propenyl[E/Z=1/9])-2,2-dimethylcyclopropanecarboxylate (hereinafter, referred to as the present ester compound A) is used as the present ester compound.

Formulation Example 2

Into an aerosol container, 0.01 parts of the present ester compound A, 0.09 parts of the diethyl adipate, and 39.9 parts of Isopar M (isoparaffin-based hydrocarbon, manufactured by Exxon Mobil Corporation) are placed. A valve portion is attached to the aerosol container, and 60 parts of a propellant (liquefied petroleum gas) is filled therein via the valve portion to obtain an aerosol.

Formulation Example 3

Into an aerosol container, 0.02 parts of the present ester compound A, 0.06 parts of the diethyl adipate, and 59.92 parts of Isopar M (isoparaffin-based hydrocarbon, manufactured by Exxon Mobil Corporation) are placed. A valve portion is attached to the aerosol container, and 40 parts of a propellant (liquefied petroleum gas) is filled therein via the valve portion to obtain an aerosol.

Formulation Example 4

Into an aerosol container, 0.1 parts of the present ester compound A, 0.9 parts of the diethyl adipate, 3 parts of isopropyl myristate, and 56 parts of Isopar M (isoparaffin-based hydrocarbon, manufactured by Exxon Mobil Corporation) are placed. A valve portion is attached to the aerosol container, and 40 parts of a propellant (liquefied petroleum gas) is filled therein via the valve portion to obtain an aerosol.

Formulation Example 5

Into an aerosol container, a solution prepared by mixing and dissolving 0.02 parts of the present ester compound A, 0.18 parts of the diethyl adipate, 8.8 parts of Isopar M (isoparaffin-based hydrocarbon, manufactured by Exxon Mobil Corporation), 0.8 parts of RHEODOL MO-60, (glyceryl oleate/propylene glycol, manufactured by Kao Corporation) and 0.2 parts of RHEODOL TW-O120 (polysorbate 80, manufactured by Kao Corporation), and 50 parts of water are placed. A valve portion is attached to the aerosol container, and 40 parts of a propellant (liquefied petroleum gas) is filled therein via the valve portion to obtain an aerosol.

Formulation Example 6

Into an aerosol container, a solution prepared by mixing and dissolving 0.02 parts of the present ester compound A, 0.06 parts of the diethyl adipate, 8.92 parts of Isopar M (isoparaffin-based hydrocarbon, manufactured by Exxon Mobil Corporation), 0.8 parts of RHEODOL MO-60 (glyceryl oleate/propylene glycol, manufactured by Kao Corporation) and 0.2 parts of RHEODOL TW-O120 (polysorbate 80, manufactured by Kao Corporation), and 50 parts of water are placed. A valve portion is attached to the aerosol container, and 40 parts of a propellant (liquefied petroleum gas) is filled therein via the valve portion to obtain an aerosol.

Formulation Example 7

Into an aerosol container, 0.02 parts of the present ester compound A, 0.18 parts of the diethyl adipate, and 49.8 parts of NEO-CHIOZOL (liquid paraffin, manufactured by Chuo Kasei Co., Ltd.) are placed. A valve portion is attached to the aerosol container, and 50 parts of a propellant (1/1 mixture of dimethyl ether/liquefied petroleum gas) is filled therein via the valve portion to obtain an aerosol.

Formulation Example 8

Into an aerosol container, 0.02 parts of the present ester compound A, 0.06 parts of the diethyl adipate, and 49.92 parts of NEO-CHIOZOL (liquid paraffin, manufactured by Chuo Kasei Co., Ltd.) are placed. A valve portion is attached to the aerosol container, and 50 parts of a propellant (1/1 mixture of dimethyl ether/liquefied petroleum gas) is filled therein via the valve portion to obtain an aerosol.

Formulation Example 9

Into an aerosol container, 0.1 parts of the present ester compound A, 0.9 parts of the diethyl adipate, 6 parts of isopropyl myristate, and 23 parts of NEO-CHIOZOL (liquid paraffin, manufactured by Chuo Kasei Co., Ltd.) are placed. A valve portion is attached to the aerosol container, and 70 parts of a propellant (1/1 mixture of dimethyl ether/liquefied petroleum gas) is filled therein via the valve portion to obtain an aerosol.

Formulation Example 10

Into an aerosol container, a solution prepared by mixing and dissolving 0.02 parts of the present ester compound A, 0.18 parts of the diethyl adipate, 5.8 parts of NEO-CHIOZOL (liquid paraffin, manufactured by Chuo Kasei Co., Ltd.), 3 parts of isopropyl myristate, 0.8 parts of RHEODOL MO-60 (glyceryl oleate/propylene glycol, manufactured by Kao Corporation) and 0.2 parts of RHEODOL TW-O120 (polysorbate 80, manufactured by Kao Corporation), and 40 parts of water are placed. A valve portion is attached to the aerosol container, and 50 parts of a propellant (1/1 mixture of dimethyl ether/liquefied petroleum gas) is filled therein via the valve portion to obtain an aerosol.

Formulation Example 11

Into an aerosol container, a solution prepared by mixing and dissolving 0.02 parts of the present ester compound A, 0.06 parts of the diethyl adipate, 5.92 parts of NEO-CHIOZOL (liquid paraffin, manufactured by Chuo Kasei Co., Ltd.), 3 parts of isopropyl myristate, 0.8 parts of RHEODOL MO-60 (glyceryl oleate/propylene glycol, manufactured by Kao Corporation) and 0.2 parts of RHEODOL TW-O120 (polysorbate 80, manufactured by Kao Corporation), and 40 parts of water are placed. A valve portion is attached to the aerosol container, and 50 parts of a propellant (1/1 mixture of dimethyl ether/liquefied petroleum gas) is filled therein via the valve portion to obtain an aerosol.

Formulation Example 12

Into an aerosol container, a solution prepared by mixing and dissolving 0.1 parts of the present ester compound A, 0.9 parts of the diethyl adipate, 8 parts of Isopar M (isoparaffin-based hydrocarbon, manufactured by Exxon Mobil Corporation), 0.9 parts of RHEODOL SP-O10 (sorbitan oleate, manufactured by Kao Corporation) and 0.1 parts of RHEODOL TW-O120 (polysorbate 80, manufactured by Kao Corporation), and a solution prepared by mixing and dissolving 69.86 parts of water and 0.14 parts of sodium benzoate are placed. A valve portion is attached to the aerosol container, and 20 parts of a propellant (liquefied petroleum gas) is filled therein via the valve portion to obtain an aerosol.

Formulation Example 13

Twenty eight parts of an ethylene-methyl methacrylate copolymer (ratio of methyl methacrylate in the copolymer: 25% by weight, product name: Acryft WK307, manufactured by Sumitomo Chemical Co., Ltd.), 2.5 parts of the present ester compound A, and 2.5 parts of the diethyl adipate are melted and kneaded using a closed-type pressure kneader (manufactured by Moriyama Company, Ltd.). The kneaded product to be obtained is hot-cut while being extruded from an extruder, to obtain a pellet. Thirty three parts of this pellet and 67 parts of a pellet of linear low density polyethylene (homopolymer of ethylene) are mixed and kneaded to obtain a resin kneaded product. Then, the resin kneaded product is extruded via heterogenous dies for net molding from an extruder and then stretched, to obtain a cylindrical molded product having a diameter of about 7 cm, made of a net of approximate rhombuses with a side of about 5 mm is formed (wherein a filament forming the net has a diameter of about 0.83 mm and an opening ratio of 82%). The molded product is cut into a length of 20 cm to obtain a vermin control composition.

Formulation Example 14

Twenty parts of the present ester compound A, 5 parts of the diethyl adipate, 3 parts of Newkalgen PS-P (sodium salt of naphthalene sulfonic acid formaldehyde condensate), 1 part of Newkalgen EX-70 (dioctyl sulfosuccinate sodium salt/sodium benzoate), 3 parts of Newkalgen SX-C (dodecyl benzenesulfonate sodium salt/sodium sulfate decahydrate) (Newkalgen Series: manufactured by TAKEMOTO OIL & FAT Co., Ltd.), and 68 parts of caster sugar (manufactured by Mitsui Sugar Co., Ltd.) are ground and mixed to obtain a powdery composition for an aqueous poison bait.

Formulation Example 15

To 24.8 parts of isopropyl alcohol were added 0.02 parts of the present ester compound A and 0.18 parts of the diethyl adipate and then mixed. The mixture was injected into an aerosol container, and 30.0 parts of an ammonium benzoate-ammonium buffer (prepared by adding 29% aqueous ammonia to a 1.0% w/w solution of ammonium benzoate and adjusting the mixture to pH 8.5) was further injected into the aerosol container to prepare an aerosol stock solution. Then, a valve is attached to the aerosol container and 45.0 parts of dimethyl ether is filled therein under pressure via the valve to obtain an aerosol.

Formulation Example 16

To 24.92 parts of isopropyl alcohol were added 0.02 parts of the present ester compound A and 0.06 parts of the diethyl adipate and then mixed. The mixture was injected into an aerosol container, and 30.0 parts of an ammonium benzoate-ammonium buffer (prepared by adding 29% aqueous ammonia to a 1.0% w/w solution of ammonium benzoate and adjusting the mixture to pH 8.5) was injected into the aerosol container to prepare an aerosol stock solution. Then, a valve is attached to the aerosol container and 45.0 parts of dimethyl ether was filled therein under pressure via the valve to obtain a one-component aerosol.

Formulation Example 17

Twenty parts of the present ester compound A, 70 parts of the diethyl adipate, and 10 parts of [2,3,5,6-tetrafluoro-4-(methoxymethyl)phenyl]methyl 2,2-dimethyl-3-(1-propenyl)cyclopropanecarboxylate are mixed to obtain a solution.

Formulation Example 18

Into an aerosol container, 0.02 parts of the present ester compound A, 0.18 parts of the diethyl adipate, 0.02 parts of [2,3,5,6-tetrafluoro-4-(methoxymethyl)phenyl]methyl 2,2-dimethyl-3-(1-propenyl)cyclopropanecarboxylate, 3 parts of isopropyl myristate, and 56.78 parts of Isopar M (isoparaffin-based hydrocarbon, manufactured by Exxon Mobil Corporation) are placed. A valve portion is attached to the aerosol container, and 40 parts of a propellant (liquefied petroleum gas) is filled therein via the valve portion to obtain an aerosol.

Formulation Example 19

Into an aerosol container, 0.02 parts of the present ester compound A, 0.18 parts of the diethyl adipate, 0.02 parts of [2,3,5,6-tetrafluoro-4-(methoxymethyl)phenyl]methyl 2,2-dimethyl-3-(1-propenyl)cyclopropanecarboxylate, 6 parts of isopropyl myristate, and 23.78 parts of NEO-CHIOZOL (liquid paraffin, manufactured by Chuo Kasei Co., Ltd.) are placed. A valve portion is attached to the aerosol container, and 70 parts of a propellant (1/1 mixture of dimethyl ether/liquefied petroleum gas) is filled therein via the valve portion to obtain an aerosol.

Formulation Example 20

Into an aerosol container, a solution prepared by mixing and dissolving 0.02 parts of the present ester compound A, 0.18 parts of the diethyl adipate, 0.02 parts of [2,3,5,6-tetrafluoro-4-(methoxymethyl)phenyl]methyl 2,2-dimethyl-3-(1-propenyl)cyclopropanecarboxylate, 8.78 parts of Isopar M (isoparaffin-based hydrocarbon, manufactured by Exxon Mobil Corporation), 0.8 parts of RHEODOL MO-60 (glyceryl oleate/propylene glycol, manufactured by Kao Corporation) and 0.2 parts of RHEODOL TW-O120 (polysorbate 80, manufactured by Kao Corporation), and 40 parts of water are placed. A valve portion is attached to the aerosol container, and 50 parts of a propellant (liquefied petroleum gas) is filled therein via the valve portion to obtain an aerosol.

Formulation Example 21

Into an aerosol container, a solution prepared by mixing and dissolving 0.02 parts of the present ester compound A, 0.18 parts of the diethyl adipate, 0.02 parts of [2,3,5,6-tetrafluoro-4-(methoxymethyl) phenyl]methyl 2,2-dimethyl-3-(1-propenyl)cyclopropanecarboxylate, 8.78 parts of Isopar M (isoparaffin-based hydrocarbon, manufactured by Exxon Mobil Corporation), 0.9 parts of RHEODOL SP-O10 (sorbitan oleate, manufactured by Kao Corporation) and 0.1 parts of RHEODOL TW-O120 (polysorbate 80, manufactured by Kao Corporation), and a solution prepared by mixing and dissolving 69.86 parts of water and 0.14 parts of sodium benzoate are placed. A valve portion is attached to the aerosol container, and 20 parts of a propellant (liquefied petroleum gas) is filled therein via the valve portion to obtain an aerosol.

Formulation Example 22

To 24.78 parts of isopropyl alcohol are added 0.02 parts of the present ester compound A, 0.18 parts of the diethyl adipate, and 0.02 parts of [2,3,5,6-tetrafluoro-4-(methoxymethyl)phenyl]methyl 2,2-dimethyl-3-(1-propenyl)cyclopropanecarboxylate, and then mixed. The mixture is injected into an aerosol container, and 30.0 parts of an ammonium benzoate-ammonium buffer (prepared by adding 29% aqueous ammonia to a 1.0% w/w solution of ammonium benzoate and adjusting the mixture to pH 8.5) is further injected into the aerosol container to prepare an aerosol stock solution. Then, a valve was attached to the aerosol container and 45.0 parts of dimethyl ether is filled therein under pressure via the valve to obtain an aerosol.

Next, the following test examples show that the pest control composition of the present invention has an excellent controlling effect on pests.

The pest control compositions of the present invention used in test examples are shown in Table 1.

TABLE 1

| | Composition (parts by weight) | |
|---|---|---|
| | Present ester compound A | Diethyl adipate |
| Present composition (1) | 10 | 90 |
| Present composition (2) | 30 | 70 |

Next, pest control compositions for comparison are shown in Table 2.

TABLE 2

| | Composition (parts by weight) | | | | |
|---|---|---|---|---|---|
| | Present ester compound A | Xylene | Ethanol | Isopropyl myristate | Diisopropyl adipate |
| Comparative composition (1) | 50 | 50 | | | |
| Comparative composition (2) | 50 | | 50 | | |
| Comparative composition (3) | 10 | | | 90 | |
| Comparative composition (4) | 30 | | | 70 | |
| Comparative composition (5) | 10 | | | | 90 |

Test Example 1

Each of the present compositions (1) and (2) and the comparative compositions (3) and (4) in a predetermined amount was diluted with deodorized kerosene (Isopar M, manufactured by Exxon Mobil Corporation), to prepare 100 parts of a liquid composition containing 0.00625% (wt/v) of the present ester compound A.

Ten imagoes of *Musca domestica* (5 male and 5 female) were released in a polyethylene cup (lower part diameter: 10.6 cm, upper part diameter: 12 cm, height: 7 cm), and the cup was closed with a 16 mesh nylon gauze. The cup was placed on the bottom part of a test chamber (bottom surface: 46 cm×46 cm, height: 70 cm). From a height of 30 cm above the upper side of the cup, 0.5 mL of the liquid composition was sprayed using a spray gun (spraying pressure: 0.9 kg/cm2). Immediately after spraying, the cup was taken out from the test chamber, and after a given period of time, the number of insects knocked down was counted and a knock down rate was calculated (average of two runs). The results are shown in Table 3.

TABLE 3

| | Knock down rate after 45 seconds (%) |
|---|---|
| Present composition (1) | 70 |
| Present composition (2) | 70 |
| Comparative composition (3) | 30 |
| Comparative composition (4) | 35 |

Test Example 2

Each of the present compositions (1) and (2) and the comparative compositions (3) to (5) in a predetermined amount was diluted with deodorized kerosene (Isopar M, manufactured by Exxon Mobil Corporation), to prepare 100 parts of a liquid composition containing 0.00625% (wt/v) of the present ester compound A.

Ten imagoes of *Blattella germanica* (5 male and 5 female) were released in a test container (diameter: 8.75 cm, height: 7.5 cm, bottom surface: 16 mesh wire netted) of which the inner wall was smeared with butter. The container was placed on the bottom part of a test chamber (bottom surface: 46 cm×46 cm, height: 70 cm). From a height of 60 cm above the upper side of the container, 1.5 mL of the liquid composition was sprayed using a spray gun (spraying pressure: 0.42 kg/cm2). Thirty seconds after spraying, the container was taken out from the test chamber, and after a given period of time, the number of insects knocked down was counted and a knock down rate was calculated (average of two runs). The results are shown in Table 4.

TABLE 4

| | Knock down rate after 0.7 minutes (%) |
|---|---|
| Present composition (1) | 65 |
| Present composition (2) | 80 |
| Comparative composition (3) | 35 |
| Comparative composition (4) | 40 |
| Comparative composition (5) | 35 |

Test Example 3

Each of the present compositions (1) and (2) and the comparative composition (2) was diluted with and dissolved in 10 parts of dichloromethane, and deodorized kerosene (Isopar M, manufactured by Exxon Mobil Corporation) was further added thereto, to prepare 100 parts of a liquid composition containing 0.00625% (wt/v) of the present ester compound A.

Ten imagoes of Musca domestica (5 male and 5 female) were released in a polyethylene cup (lower part diameter: 10.6 cm, upper part diameter: 12 cm, height: 7 cm), and the cup was closed with a 16 mesh nylon gauze. The cup was placed on the bottom part of a test chamber (bottom surface: 46 cm×46 cm, height: 70 cm). From a height of 30 cm above the upper side of the cup, 0.5 mL of the liquid composition was sprayed using a spray gun (spraying pressure: 0.9 kg/cm2). Immediately after spraying, the cup was taken out from the test chamber, and after a given period of time, the number of insects knocked down was counted and a knock down rate was calculated (average of two runs). The results are shown in Table 5.

TABLE 5

|  | Knock down rate after 45 seconds (%) |
| --- | --- |
| Present composition (1) | 70 |
| Present composition (2) | 75 |
| Comparative composition (2) | 20 |

Test Example 4

Each of the present compositions (1) and (2) and the comparative compositions (1) and (2) in a predetermined amount was diluted with and dissolved in 10 parts of dichloromethane, and deodorized kerosene (Isopar M, manufactured by Exxon Mobil Corporation) was further added thereto, to prepare 100 parts of a liquid composition containing 0.00625% (wt/v) of the present ester compound A.

Ten imagoes of Blattella germanica (5 male and 5 female) were released in a test container (diameter: 8.75 cm, height: 7.5 cm, bottom surface: 16 mesh wire netted) of which the inner wall was smeared with butter. The container was placed on the bottom part of a test chamber (bottom surface: 46 cm×46 cm, height: 70 cm). From a height of 60 cm above the upper side of the container, 1.5 mL of the liquid composition was sprayed using a spray gun (spraying pressure: 0.9 kg/cm2). Thirty seconds after spraying, the container was taken out from the test chamber, and after a given period of time, the number of insects knocked down was counted and a knock down rate was calculated (average of two runs). The results are shown in Table 6.

TABLE 6

|  | Knock down rate after 0.7 minutes (%) |
| --- | --- |
| Present composition (1) | 80 |
| Present composition (2) | 70 |
| Comparative composition (1) | 35 |
| Comparative composition (2) | 10 |

INDUSTRIAL APPLICABILITY

The pest control composition of the present invention has an excellent control effect on pests and is useful.

The invention claimed is:

1. A method for controlling pests comprising applying a pest control composition to pests or habitats of pests, the pest control composition comprising an ester compound represented by formula (1)

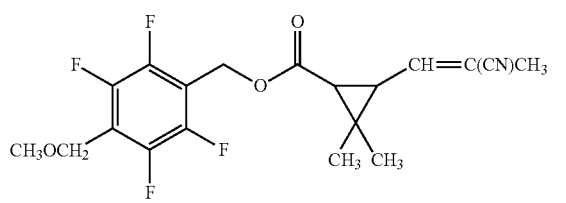

(1)

and diethyl adipate, and wherein the pests are Dictyoptera vermin.

2. The method for controlling pests according to claim 1, wherein a content ratio of the ester compound represented by the formula (1) to the diethyl adipate is from 4:1 to 1:300 by weight ratio.

3. The method for controlling pests according to claim 1, wherein the content ratio of the ester compound represented by the formula (1) to the diethyl adipate is from 1:1 to 1:100 by weight ratio.

* * * * *